(12) United States Patent
Johnson et al.

(10) Patent No.: US 10,899,686 B2
(45) Date of Patent: Jan. 26, 2021

(54) PROCESS FOR THE PREPARATION OF 2,3,3,3-TETRAFLUOROPROPENE (1234YF)

(71) Applicant: MEXICHEM FLUOR S.A. DE C.V., San Luis Potosi (MX)

(72) Inventors: Sheryl Louise Johnson, Cheshire (GB); Stephen Andrew Flaherty, Cheshire (GB); James Henry Murray, Cheshire (GB); Fiona Louise Smith, Cheshire (GB); Jonathan Junhay Man, Cheshire (GB); Clive Robert Giddis, Cheshire (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 357 days.

(21) Appl. No.: 15/745,505

(22) PCT Filed: Jul. 14, 2016

(86) PCT No.: PCT/GB2016/052145
§ 371 (c)(1),
(2) Date: Jan. 17, 2018

(87) PCT Pub. No.: WO2017/013406
PCT Pub. Date: Jan. 26, 2017

(65) Prior Publication Data
US 2020/0165179 A1   May 28, 2020

(30) Foreign Application Priority Data

Jul. 17, 2015   (GB) .................................... 1512593.3

(51) Int. Cl.
*C07C 17/357*   (2006.01)
*B01J 23/26*   (2006.01)
(Continued)

(52) U.S. Cl.
CPC ............. *C07C 17/357* (2013.01); *B01J 23/06* (2013.01); *B01J 23/26* (2013.01); *C07C 17/206* (2013.01); *C07C 17/383* (2013.01); *C07C 21/185* (2013.01)

(58) Field of Classification Search
CPC ..... C07C 17/383; C07C 17/25; C07C 17/206; C07C 21/18; C07C 19/08; C07C 17/38;
(Continued)

(56) References Cited

U.S. PATENT DOCUMENTS 9,890,096 B2   2/2018   Cottrell et al.
2007/0100175 A1   5/2007   Miller et al.
(Continued)

FOREIGN PATENT DOCUMENTS

CN   103055643   4/2013
CN   103534228 A   1/2014
(Continued)

OTHER PUBLICATIONS

International Search Report pertaining to PCT/GB2016/052145, dated Oct. 31, 2016, 3 pages.
(Continued)

*Primary Examiner* — Jafar F Parsa
(74) *Attorney, Agent, or Firm* — Brinks Gilson & Lione; Yuezhong Feng

(57) ABSTRACT

The present invention provides an integrated process for preparing 2,3,3, 3-tetrafluoropropene (1234yf), the process comprising: (a) vapour phase catalytic fluorination of a first composition comprising 3,3,3-trifluoro-2-chloro-prop-1-ene (CF3C—CNCH2, 1233xf) with hydrogen fluoride (HF) in a fluorination reactor to produce a fluorination product stream comprising 1,1,2,2-pentafluoropropane (245cb), HF and HCl; (b) vapour phase catalytic dehydrofluorination composition comprising 245cb in a dehydrofluorination reactor
(Continued)

to produce a dehydrofluorination product stream comprising 1234yf and HF; wherein the fluorination product stream and the dehydrofluorination product stream are combined and subjected to (c) purification to produce a composition comprising 245cb and a 1234yf product stream.

20 Claims, 1 Drawing Sheet

(51) Int. Cl.
*C07C 17/20* (2006.01)
*B01J 23/06* (2006.01)
*C07C 17/383* (2006.01)
*C07C 21/185* (2006.01)

(58) Field of Classification Search
CPC . B01J 23/866; B01J 37/12; B01J 37/24; B01J 27/26; B01J 27/132
See application file for complete search history.

(56) References Cited

U.S. PATENT DOCUMENTS

| | | | |
|---|---|---|---|
| 2009/0240090 A1 | 9/2009 | Merkel et al. | |
| 2012/0184785 A1 | 7/2012 | Cottrell et al. | |
| 2014/0275653 A1 | 9/2014 | Pigamo et al. | |
| 2015/0203422 A1* | 7/2015 | Deur-Bert | C01B 7/191 570/156 |

FOREIGN PATENT DOCUMENTS

| | | |
|---|---|---|
| EP | 0502605 | 9/1992 |
| EP | 0773061 | 5/1997 |
| EP | 0967074 | 12/1999 |
| JP | 2009227675 | 10/2009 |
| WO | WO1998/010862 | 3/1998 |
| WO | WO2006/106353 | 10/2006 |
| WO | WO2007/053178 | 5/2007 |
| WO | WO2007/053736 | 5/2007 |
| WO | WO2007/079431 | 7/2007 |
| WO | WO2007/079435 | 7/2007 |
| WO | WO2008/008350 | 1/2008 |
| WO | WO2008/040969 | 4/2008 |
| WO | WO2008/054781 | 5/2008 |
| WO | WO2008/054782 | 5/2008 |
| WO | WO2008/057794 | 5/2008 |
| WO | WO2008/075017 | 6/2008 |
| WO | WO2009/003084 | 12/2008 |
| WO | WO2009/003157 | 12/2008 |
| WO | WO2009/026526 | 2/2009 |
| WO | WO 2009/026526 | 2/2009 |
| WO | WO2009/105512 | 8/2009 |
| WO | WO2009/125199 | 10/2009 |
| WO | WO 2009/125199 | 10/2009 |
| WO | WO2010/001025 | 1/2010 |
| WO | WO2010/059493 | 5/2010 |
| WO | WO2010/116150 | 10/2010 |
| WO | WO2010/123154 | 10/2010 |
| WO | WO2011/077191 | 6/2011 |
| WO | WO2011/077192 | 6/2011 |
| WO | WO2011/077193 | 6/2011 |
| WO | WO2011/099604 | 8/2011 |
| WO | WO2011/099605 | 8/2011 |
| WO | WO2011/139646 | 11/2011 |
| WO | WO2011/140013 | 11/2011 |
| WO | WO2012/052797 | 4/2012 |
| WO | WO2012/057367 | 5/2012 |
| WO | WO2012/098421 | 7/2012 |
| WO | WO2012/098422 | 7/2012 |
| WO | WO2012/121876 | 9/2012 |
| WO | WO2013/015068 | 1/2013 |
| WO | WO2013/045791 | 4/2013 |
| WO | WO2013/067350 | 5/2013 |
| WO | WO2013/067356 | 5/2013 |
| WO | WO2013/074324 | 5/2013 |
| WO | WO2013/088195 | 6/2013 |
| WO | WO2013/130385 | 9/2013 |
| WO | WO2013/164618 | 11/2013 |
| WO | WO2013/184865 | 12/2013 |

OTHER PUBLICATIONS

R M Joyce et al., J. Am. Chem. Soc., 70, 2529 (1948) (4 pgs).
Zang, L., "Patented 1234yf Production Techniques of US Companies", Chemical Enterprise Management, 2015, 25, 214 (Four pages including English translation).

* cited by examiner

PROCESS FOR THE PREPARATION OF 2,3,3,3-TETRAFLUOROPROPENE (1234YF)

The present invention is concerned with the preparation of 2,3,3,3-tetrafluoropropene (1234yf). More particularly, the present invention is concerned with an integrated process for the preparation of 2,3,3,3-tetrafluoropropene (1234yf) comprising fluorinating 3,3,3-trifluoro-2-chlor-prop-1-ene ($CF_3CCl=CH_2$, 1233xf) and dehydrofluorinating 1,1,1,2,2-pentafluoropropane ($CF_3CF_2CH_3$, 245cb).

Hereinafter, unless otherwise stated, 2,3,3,3-tetrafluoropropene will be referred to as 1234yf. 1234yf is known to have utility as, for example, a refrigerant, foam blowing agent, aerosol propellant or a heat transfer media. 1234yf has zero Ozone Depletion Potential (ODP) and very low Global Warming Potential (GWP).

There are methods known in the art for producing 1234yf. However, these can suffer from disadvantages such as low yields, and/or the handling of toxic and/or expensive reagents, and/or the use of extreme conditions, and/or the production of toxic by-products.

There is a need for a more economically efficient means for producing 1234yf. In particular, there is a need to provide a process in which unused starting materials and/or intermediate reaction products are recycled into the process and/or commercially valuable by-products are recovered so that they may be sold or used in another economically valuable way.

The listing or discussion of a prior-published document in this specification should not necessarily be taken as an acknowledgement that the document is part of the state of the art or is common general knowledge.

The present invention provides an integrated process for preparing 2,3,3,3-tetrafluoropropene (1234yf), the process comprising:

(a) vapour phase catalytic fluorination of a first composition comprising 3,3,3-trifluoro-2-chloro-prop-1-ene ($CF_3CCl=CH_2$, 1233xf) with hydrogen fluoride (HF) in a fluorination reactor to produce a fluorination product stream comprising 1,1,1,2,2-pentafluoropropane (245cb), HF and HCl;

(b) vapour phase catalytic dehydrofluorination of a second composition comprising 245cb in a dehydrofluorination reactor to produce a dehydrofluorination product stream comprising 1234yf and HF;

wherein the fluorination product stream and the dehydrofluorination product stream are combined and subjected to (c) purification to produce a composition comprising 245cb and a 1234yf product stream.

The present inventors have found that combining the fluorination product stream and the dehydrofluorination product stream prior to the purification step (c) allows for efficient purification of reactor products and recycle of unreacted starting materials such as HF can be particularly efficient.

The purification step (c) may comprise one or more purification steps. Any suitable purification method may be used. Suitable purification methods include but are not limited to distillation, phase separation, adsorption, e.g. using molecular sieves and/or activated carbon, and scrubbing. Purification step (c) may comprise one or more distillation steps and/or one or more scrubbing trains and/or one or more phase separation steps and/or one or more adsorption steps, e.g. using molecular sieves and/or activated carbon.

In one aspect, purification step (c) may comprise one or more distillation steps and one or more scrubbing steps.

As an example, the purification step (c) may comprise one or more distillation steps, followed by one or more scrubbing steps, followed by one or more distillation steps.

If, for example, the purification step (c) comprises distillation followed by scrubbing, the lighter fraction removed from a distillation column may be passed to a scrubbing train.

Scrubbing techniques are known in the art. Typically the scrubbing will remove inorganic impurities such as hydrogen fluoride, hydrogen chloride or water. Any suitable scrubbing technique may be used, such as scrubbing with water, or absorption into an acid stream. When the scrubbing uses an aqueous medium, the last stage of the scrubbing train will preferably comprise a drying step, for example contacting with concentrated sulphuric acid, or drying with molecular sieves.

Impurities, by products and unused starting materials that are removed during the purification step (c) may be purified and stored for future use or may be recycled into the process of the invention. For example, HF removed during the purification step (c) may be recycled for use in reaction step (a). If necessary, the HF may be purified before it is recycled. Any suitable method may be used to purify HF. An example of a suitable method is phase separation.

The composition comprising 245cb and a 1234yf product stream obtained in purification step (c) may be fed to the dehydrofluorination reactor as the second composition.

In one aspect, at least some of the 1234yf is removed from the composition comprising 245cb and a 1234yf product stream and the resulting composition is fed to the dehydrofluorination reactor as the second composition. The 1234yf that is removed may be collected and stored. If necessary the 1234yf may be further purified before it is collected and stored, but a situation in which this is not necessary is envisaged.

The 1234yf may be removed and recovered using any suitable separation method. One suitable method is distillation.

Optionally, if the composition comprising 245cb and a 1234yf product stream comprises some 1234ze(E), at least some of the 1234ze(E) may be removed from the composition. As an example, after at least some of the 1234yf has been removed, the resulting composition may be subjected to a purification step in which at least some of any 1234ze that may be present in the composition is removed before the composition is fed to the dehydrofluorination reactor as the second composition.

The 1234ze(E) may be removed and recovered using any suitable separation method. One suitable method is distillation.

The following is a non-limiting example of a purification process (c) as used in the present invention. The fluorination product stream and the dehydrofluorination product stream are both feed into a first distillation still. Lighter/lower boiling components of the feed mixture (including 245cb, 1234yf, 1234ze(E), and some HF) are distilled from the mixture leaving a heavier/higher boiling fraction (including the majority of the HF and unreacted 1233xf), which in a preferred embodiment may be recycled. The distilled (lower boiling) components are passed into a scrubbing train.

This scrubbing train may contain one or more scrubbers. Suitable scrubbers include, but are not limited to, one or more water scrubbers, one or more basic scrubbers using sodium hydroxide or potassium hydroxide and one or more acid scrubbers such as sulphuric acid scrubbers and combinations thereof. In one example, the distillate passes through a water scrubber (to remove bulk acid), then a basic scrubber (to remove trace acid), than a sulphuric acid scrubber (to remove water). Effluent is removed from the scrubbers and a stream comprising 245cb and a 1234yf product stream essentially free of acid and water exits the scrubber train for further purification.

In preferred embodiments, the scrubbing train includes, in sequence, a bulk acid removal step, a trace acid removal step and one or more drying steps.

The bulk acid removal step may comprise contacting the stream to be purified with a stream of water, for example in a quantity sufficient to provide an effluent stream having a HF concentration of around 5 wt %. In alternative embodiments, the bulk acid removal step may comprise contacting the stream to be purified with a stream of aqueous HF, for example in a concentration of around 50 wt % to produce an effluent stream having an HF concentration in the region of 70 wt %.

The trace acid removal step preferably comprises contacting the stream to be purified, after the bulk acid removal step, with a stream of aqueous caustic, for example NaOH or KOH (i.e. a basic scrubbing step). The NaOH or KOH preferably has a concentration of around 20 wt % or less, for example less than 10 wt % or less than 5 wt %.

In some embodiments, the drying step includes contacting the product stream with a source of sulphuric acid, preferably in a concentration of around 78 wt % to around 98 wt %, more preferably in a concentration between about 80 wt % and about 94 wt %. In some embodiments, the drying step includes a first drying stage in which the product stream is contacted with a first source of sulphuric acid followed by a second drying stage where the product stream is contacted with a second source of sulphuric acid. In such embodiments, the first source of sulphuric acid preferably has a concentration between about 78 wt % and about 90 wt %, while the second source of sulphuric acid has a concentration between about 90 wt % and about 98 wt %, e.g. about 90 wt % to about 94 wt %. Such an arrangement allows for effective drying of the product stream while also minimising the presence of degradation products in the scrubbing effluent.

In an alternative embodiment, the acid removal step comprises contacting the crude product stream with a source of aqueous acid, e.g. a source of aqueous HF and/or HCl. Preferably, the source of aqueous acid comprises aqueous HF in a concentration of at least about 40 wt %, for example in a concentration of at least about 50 wt %. In certain embodiments, HF and/or HCl is recovered from the spent stream of aqueous acid, for example by flash separation and/or distillation.

The stream comprising 245cb and 1234yf passes into a second still. In this second still, lower boiling impurities such as 1,1,1-trifluoropropyne [known hereafter as trifluoromethylacetylene, TFMA] are removed and the fraction containing higher boiling components such as 245cb, 1234yf and optionally 1234ze(E) is recovered for further purification or recycling into the reaction process; this fraction is the composition comprising 245cb and a 1234yf product stream.

The composition comprising 245cb and a 1234yf product stream leaving the purification step (c) can be recycled into the reaction process and/or can be further purified. In a preferred aspect, this product of the purification step (c) is subjected to a further (third) distillation step. In this distillation step, 1234yf (the desired product) can be isolated as the distillate. The heavier/higher boiling fraction contains 245cb as the major component, but may also comprise 1234ze(E). If 1234ze(E) is present, this may optionally be isolated in a further (fourth) distillation step, by removing 245cb as the distillate. The 245cb containing stream from the third or fourth distillation step can then be passed to the dehydrofluorination reactor. Additional distillation steps may be added as required to remove undesired impurities.

Step (a) is carried out in the gas phase. It preferably is conducted at a temperature of from about 0 to about 390° C., such as from about 100 to about 350° C. or from about 200 to about 300° C. or from about 300° C. to about 350° C., such as about 350° C. and conducted at a pressure of from about 0.1 to about 30 bara (about 10 kPa to about 3000 kPa) or about 0.5 to about 25 bare (about 50 kPa to about 2500 kPa), such as from about 1 to about 20 bara (about 100 to about 2000 kPa), for example about 5 to about 15 bara (about 500 to about 1500 kPa).

In reactor (a), the molar ratio of HF to 1233xf is typically from about 1:1 to about 20:1, or about 5:1 to about 15:1, or about 7:1 to about 12:1, for example about 8:1 or about 9:1 or about 10:1.

In one aspect, reaction (a) takes place in the presence of air. When this reaction takes place in the presence of air, the molar ratio of air to 1233xf is typically from about 0.1:1 to about 1:1, or about 0.2:1 to about 0.8:1, or about 0.3:1 to about 0.6:1, such as about 0.4:1 or about 0.5:1.

Reaction (a) takes place in the presence of a catalyst. Suitable catalysts chromium oxyfluoride catalysts of the formula CrOF, which may contain an additional metal selected from Zr, Co, Ni, Mu and/or Mg, which may be supported or unsupported. Preferred catalysts include zinc/chromia catalysts. Suitable catalysts are described in WO2011/140013 and US2014/0275653, which are herein incorporated by reference.

The catalysts used in the invention may be prepared from a commercial fluorinated chromium compound as the catalyst precursor. Any suitable fluorinated chromium compound may be used, for example, $CrF_3 \cdot xH_2O$, $Cr/Ni/AlF_3$ or fluorinated $Cr_2O_3$. The chromium fluoride compound may be anhydrous or hydrated, but is preferably hydrated. The fluorinated chromium compound, such as $CrF_3 \cdot xH_2O$, is first calcined. The calcination may occur under any suitable conditions. As an example, during calcination, the chromium fluoride may be heated to a temperature of from about 200 to about 1000° C., such as from about 400 to about 500° C. The chromium fluoride may be heated in an atmosphere of at least one inert gas, such as nitrogen, helium, or argon. For example, the chromium fluoride may be heated in a stream of nitrogen to calcine the catalyst precursor. It is also possible to calcine the hydrated chromium fluoride using an active gas (a gas capable of reacting, such as air). The inert gas or active gas may be pre-heated or the reactor may be heated once the catalyst precursor and the inert gas are contained therein. A contact time between the heated inert gas/or active gas and the catalyst precursor may be from about 10 to about 200 seconds, such as from about 10 to 100 seconds, or from about 20 to about 50 seconds. The pressure is typically from about 105 KPa to about 1.5 KPa.

Alternatively, the catalyst may be produced by activating a chromium-containing compound, such as $Cr_2O_3$, with hydrogen fluoride to form an activated chromium oxyfluoride.

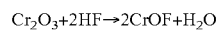

$Cr_2O_3 + 2HF \rightarrow 2CrOF + H_2O$

The catalyst may be unsupported or supported. Suitable supports include, but are not limited to activated carbon, graphite, or their corresponding HF-activated compounds, such as fluorinated graphite, or fluorinated alumina. For example, $CrF_3$, or CrOF, may be supported on alumina.

The physical shape of the catalyst is not particularly limited. The catalyst may, for example, be in the shape of pellets or granules. The catalyst may be combined with other ingredients, such as graphite, which may function as a bonding agent for making stronger pellets and/or to operate under pressure without attrition. Additionally, for supported catalysts, the supports may also be in the form of granules or pellets, or the like.

By the term "zinc/chromia catalyst" we mean any catalyst comprising chromium or a compound of chromium and zinc or a compound of zinc. Such catalysts are known in the art, see for example EP-A-0502605, EP-A-0773061, EP-A-0957074, WO 2010/116150 and WO 98/10862, which are all hereby incorporated by reference.

Typically, the chromium or compound of chromium present in the zinc/chromia catalysts used in reaction (a) is an oxide, oxyfluoride or fluoride of chromium such as chromium oxide.

The total amount of the zinc or a compound of zinc present in the zinc/chromia catalysts used is typically from about 0.01% to about 25%, preferably 0.1% to about 25%, conveniently 0.01% to 6% zinc, and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst. Alternatively, the catalyst conveniently comprises 0.01% to 1%, more preferably 0.05% to 0.5% zinc.

The preferred amount depends upon a number of factors such as the nature of the chromium or a compound of chromium and/or zinc or a compound of zinc and/or the way in which the catalyst is made. These factors are described in more detail hereinafter.

It is to be understood that the amount of zinc or a compound of zinc quoted herein refers to the amount of elemental zinc, whether present as elemental zinc or as a compound of zinc.

The zinc/chromia catalysts may include an additional metal or compound thereof. Typically, the additional metal is a divalent or trivalent metal, preferably selected from nickel, magnesium, aluminium and mixtures thereof. Typically, the additional metal is present in an amount of from 0.01% by weight to about 25% by weight of the catalyst, preferably from about 0.01 to 10% by weight of the catalyst. Other embodiments may comprise at least about 0.5% by weight or at least about 1% weight of additional metal.

The zinc/chromia catalysts may be amorphous. By this we mean that the catalyst does not demonstrate substantial crystalline characteristics when analysed by, for example, X-ray diffraction.

Alternatively, the catalysts may be partially crystalline. By this we mean that from 0.1 to 50% by weight of the catalyst is in the form of one or more crystalline compounds of chromium and/or one or more crystalline compounds of zinc, if a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

During use in a reaction the degree of crystallinity may change. Thus it is possible that a catalyst has a degree of crystallinity as defined above before use and will have a degree of crystallinity outside these ranges during or after use in a reaction.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (e.g. the graphite used in producing catalyst pellets) or more preferably by comparison of the intensity of the XRD patterns of the sample materials with reference materials prepared from suitable internationally recognised standards, for example NIST (National Institute of Standards and Technology) reference materials.

The zinc/chromia catalysts typically have a surface area of at least 50 $m^2/g$ and preferably from 70 to 250 $m^2/g$ and most preferably from 100 to 200 $m^2/g$ before it is subjected to pre-treatment with a fluoride containing species such as hydrogen fluoride or a fluorinated hydrocarbon. During this pre-treatment, which is described in more detail hereinafter, at least some of the oxygen atoms in the catalyst are replaced by fluorine atoms.

The zinc/chromia catalysts used typically have an advantageous balance of levels of activity and selectivity. Preferably, they also have a degree of chemical robustness that means that they have a relatively long working lifetime. The zinc/chromia catalysts preferably also have a mechanical strength that enables relatively easy handling, for example they may be charged to reactors or discharged from reactors using known techniques.

The zinc/chromia catalysts may be provided in any suitable form known in the art. For example, they may be provided in the form of pellets or granules of appropriate size for use in a fixed bed or a fluidised bed. The catalysts may be supported or unsupported. If the catalyst is supported, suitable supports include $AlF_3$, fluorinated alumina or activated carbon.

The zinc/chromia catalysts include promoted forms of such catalysts, including those containing enhanced Lewis and/or Brönsted acidity and/or basicity.

In use, the catalyst, such as a zinc/chromia catalyst, may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst. Alternatively, the catalyst can be regenerated continuously whilst in use by introducing an oxidising gas into the reactor e.g. oxygen or chlorine.

The catalyst, for example the zinc/chromia catalyst, may be used in an amount of from about 0.01 to about 50% by weight, such as from about 0.1 to about 30%, for example from about 0.5 to about 20%, based on the combined weight of organics and HF.

The fluorination reaction typically takes place at a temperature of from 250° C. to 400° C., such as from 300° C. to 350° C., for example about 350° C. This reaction is typically conducted at a pressure of 100 to 2000 kPa, such as from 4 to 1800 kPa, for example about 1500 kPa.

The fluorination product stream may be subjected to a purification step to remove at least some of the HCl and at least some of the air (if present) before this product stream Is combined with the dehydrofluorination product stream.

If step (a) is conducted in the presence of air, air and HCl present in the product stream may optionally be removed by distillation before the fluorination product stream is combined with the dehydrofluorination product stream.

Even if step (a) is not conducted in the presence of air, HCl present in the product stream may optionally be removed by distillation before the fluorination product stream is combined with the dehydrofluorination product stream.

The 1233xf used in reaction (a) may be obtained by the dehydrochlorination of $CF_3CHClCH_2Cl$ (243db).

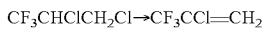

$$CF_3CHClCH_2Cl \rightarrow CF_3CCl=CH_2$$

This dehydrochlorination reaction typically takes place in a separate reactor to the fluorination reactor in which reaction (a) takes place. The dehydrochlorination reactor and the fluorination reactor may be arranged in series.

The dehydrochlorination reaction may take place in the presence of HF. If this reaction takes place in the presence of HF, the molar ratio of HF to 243db is typically from about 1:1 to about 20:1, or about 5:1 to about 15:1, or about 7:1 to about 12:1, for example about 8:1 or about 9:1 or about 10:1.

The dehydrochlorination reaction may take place in the absence of air.

The dehydrochlorination reaction may take place in the presence of a catalyst. Preferred catalysts are those comprising activated carbon, alumina and/or an oxide of a transition metal. A further group of preferred catalysts are supported (e.g. on carbon) or unsupported Lewis acid metal halides, including $TaX_5$, $SbX_5$, $SnX_4$, $TiX_4$, $FeCl_3$, $NbX_5$, $VX_5$, $AlX_3$ (wherein X=F or Cl).

For the avoidance of doubt, by catalysts comprising activated carbon, alumina and/or an oxide of a transition metal, we include catalysts that are essentially only activated carbon, alumina and/or an oxide of a transition metal and catalysts that are activated carbon, alumina and/or an oxide of a transition metal modified, for example, by the addition of one or more metals (e.g. transition metals) and/or compounds thereof.

By "activated carbon", we include any carbon with a relatively high surface area such as from about 50 to about 3000 $m^2$ or from about 100 to about 2000 $m^2$ (e.g. from about 200 to about 1500 $m^2$ or about 300 to about 1000 $m^2$). The activated carbon may be derived from any carbonaceous material, such as coal (e.g. charcoal), nutshells (e.g. coconut) and wood. Any form of activated carbon may be used, such as powdered, granulated and pelleted activated carbon. Activated carbon which has been modified (e.g. impregnated) by the addition of Cr, Mn, Au, Fe, Sn, Ta, Ti, Sb, Al, Co, Ni, Mo, Ru, Rh, Pd and/or Pt and/or a compound (e.g. a halide) of one or more of these metals may be used.

Alumina which has been modified by the addition of Cr, Mn, Au, Fe, Sn, Ta, Ti, Sb, Al, Co, Ni, Mo, Ru, Rh, Pd and/or Pt and/or a compound (e.g. a halide) of one or more of these metals may be used.

An oxide of a transition metal that has been modified by the addition of Cr, Mn, Au, Fe, Sn, Ta, Ti, Sb, Al, Co. Ni, Mo, Ru, Rh, Pd and/or Pt and/or a compound (e.g. a halide) of one or more of these metals may be used.

A preferred oxide of a transition metal is an oxide of Cr, Ti, V, Zr, or Fe. For example, chromia ($Cr_2O_3$) alone or chromia that has been modified by the addition of Zn, Mn, Zr, Ni, Al and/or Mg and/or a compound of one or more of these metals may be used. Suitable chromia-based catalysts include those described in EP-A-0502605, EP-A-0773061, EP-A-957074, WO 98/10862 and WO 2006/106353.

A preferred group of catalysts for the dehydrochlorination reaction are catalysts which comprise activated carbon, alumina and/or chromia. Catalysts based on chromia currently are particularly preferred. A preferred chromia-based catalyst is a zinc/chromia catalyst as described above.

The catalyst used in the dehydrochlorination reaction may be the same as the catalyst used in the fluorination reaction.

The catalyst in the dehydrochlorination reaction may be used in an amount of from about 0.01 to about 50% by weight, such as from about 0.1 to about 30%, for example from about 0.5 to about 20%, based on the weight of 243db.

It is preferable for the dehydrochlorination reaction to be carried out in the presence of hydrogen fluoride (HF). For example, when alumina or an oxide of a transition metal is used as a catalyst in step (e.g. a chromia-based catalyst such as a zinc/chromia catalyst), HF may be used to prevent and/or retard excessive decomposition of the catalyst.

The dehydrochlorination reaction may be carried out at a temperature of from about −70 to about 450° C. and at atmospheric, sub- or super-atmospheric pressure, preferably from about 0 to about 30 bare (about 0 to about 3000 kPa).

Preferably, the dehydrochlorination reaction is conducted at a temperature of from about 0 to about 390° C., such as from about 100 to about 380° C. or from about 200 to about 370° C. (e.g. from about 240 to about 260° C. or about 350° C.).

The dehydrochlorination reaction preferably is carried out at a pressure of from about 0.01 to about 25 bara (about 1 to about 2500 kPa) or about 0.1 to about 20 bara (about 10 to about 2000 kPa), such as from about 1 to about 10 bara (about 100 to about 1000 kPa). e.g. about 1 to about 5 bara (about 100 to about 500 kPa).

The dehydrochlorination reaction typically takes place at a temperature of from 250° C. to 400° C., such as from 300° C. to 350° C., for example about 350° C. This reaction is typically conducted at a pressure of 100 to 2000 kPa, such as from 4 to 1800 kPa, for example about 1500 kPa.

In one aspect, the temperature and pressure in the dehydrochlorination reactor is approximately the same or similar to the temperature and pressure in the fluorination reactor.

The dehydrochlorination reaction may take place in the presence of HF. In one aspect, at least part of the HF present in the dehydrochlorination reactor is recycled from step (c).

1233xf produced in the dehydrochlorination step may be transferred from the dehydrochlorination reactor directly to the fluorination reactor for step (a). However, 1233xf may be subjected to a purification step before being passed to the fluorination reactor. The purification may be achieved by separation of the 1233xf from any other products or reagents by any suitable method such as one or more distillation, condensation, adsorption, e.g. using molecular sieves and/or activated carbon, or phase separation steps and/or by scrubbing with water or aqueous base.

243db is commercially available (e.g. from Apollo Scientific Ltd, UK). Alternatively, 243db may also be prepared via a synthetic route starting from the cheap feedstocks carbon tetrachloride ($CCl_4$) and ethylene (see the reaction scheme set out below). These two starting materials may be telomerised to produce 1,1,1,3-tetrachloropropane (see, for example, J. Am. Chem. Soc. Vol. 70, p 2529, 1948, which is incorporated herein by reference) (also known as HCC-250fb, or simply 250fb).

250fb may then be fluorinated to produce 3,3,3-trifluoropropene (1243zf) and/or 1,1,1-trifluoro-3-chloropropane (e.g. using HF, optionally in the presence of a chromia-containing catalyst, preferably a zinc/chromia catalyst as described herein). Dehydrohalogenation of 1,1,1-trifluoro-3-chloropropane (e.g. using NaOH or KOH) produces 3,3,3-trifluoropropene (1243zf).

1243zf may then be readily halogenated, such as chlorinated (e.g. with chlorine) to produce 1,1,1-trifluoro-2,3-dichloropropane (243db). This reaction scheme is summarised below (minus the route from 250fb to 1243zf via 3,3,3-trichloropropene).

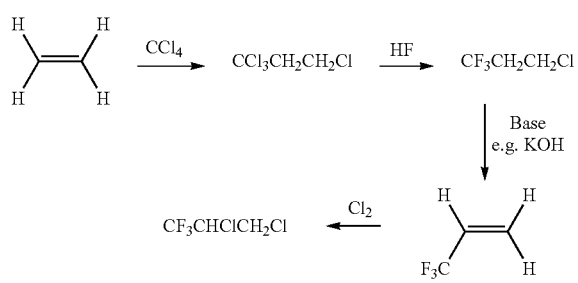

Optionally the halogenation of 1243zf can be undertaken in the same reactor as reaction (a), for example by providing a feed comprising 1243zf, HF and chlorine.

The dehydrofluorination reaction (b) typically takes place at a temperature of from about 200 to about 600° C., such as from about 220 to about 500° C., for example about 240 to 360° C., such as about 340 or about 350° C. This reaction typically takes place at a pressure of from about 0.01 to about 25 bara (about 1 to about 2500 kPa) or about 0.1 to about 20 bara (about 10 to about 2000 kPa), such as from about 1 to about 10 bara (about 100 to about 1000 kPa), e.g. about 1 to about 5 bara (about 100 to about 500 kPa), for example about 2 bar (200 kPa).

Reaction (b) takes place in the presence of a catalyst. Suitable catalysts include metal and carbon based catalysts such as those comprising activated carbon, main group (e.g. alumina-based catalysts, such as chrome on alumina catalysts) and transition metals, such as chromia-based catalysts (e.g. zinc/chromia) or nickel-based catalysts (e.g. nickel mesh). One preferred method of effecting the dehydrohalogenation uses a metal catalyst, such as a chromia-based (e.g. zinc/chromia) catalyst.

Suitable zinc/chromia catalysts include those described above. Any suitable chrome on alumina catalyst may be used. Examples of suitable chrome on alumina catalysts include those described in above and in WO 2013/164618, which is incorporated herein by reference.

The reaction time for each step (a) and (b) and the dehydrochlorination step (if used) may vary over a wide range. However, the reaction time for each step will typically be in the region of from 0.01 to 100 hours, such as from 0.1 to 50 hours, e.g. from 1 to 20 hours.

Any suitable apparatus may be used as a reactor for steps (a) and (b) and the dehydrochlorination step (if used), such as a static mixer, a stirred tank reactor or a stirred vapour-liquid disengagement vessel. Preferably, the apparatus is made from one or more materials that are resistant to corrosion, e.g. Hastelloy or Iconel.

BRIEF DESCRIPTION OF THE FIGURES

In FIG. 1, (a) is the fluorination reactor in which 1233xf is fluorinated using HF to produce a fluorination product stream comprising 245cb, HF and HCl. (I) is the optional HCl and air still or HCl still that may be used to remove HCl and air or HCl from the product stream leaving reactor (a), (b) is the dehydrofluorination reactor in which 245cb is dehydrofluorinated to produce a product stream comprising 1234yf and HF. The product streams from reactors (a) and (b) are combined and subjected to purification in step (c). IV is an optional step for the purification or separation of HF and unreacted 1233xf before recycle for use in reactor (a).

IV may, for example, be conducted in a phase separator. II is an optional step for the separation of 1234yf. II may, for example, be conducted in a distillation still. III is an optional step for the separation of 1234ze(E). III may, for example, be conducted in a distillation still.

Figure 2:
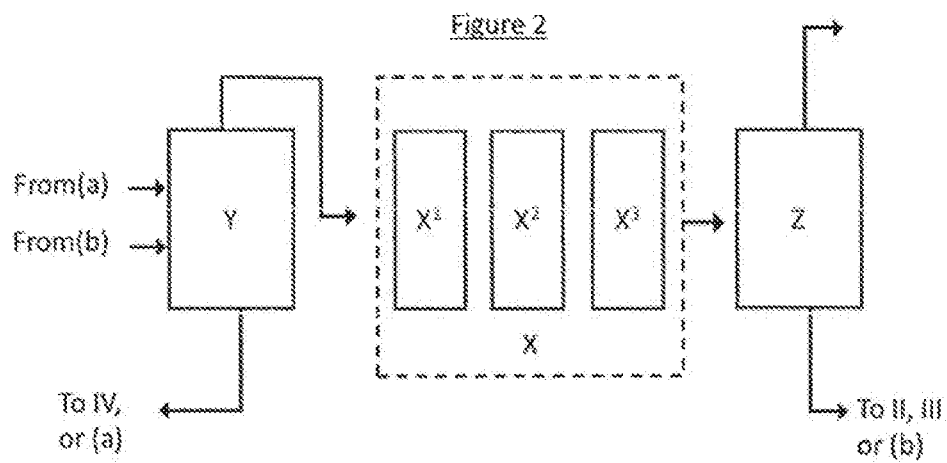

FIG. 2. provides a schematic representation of one possible arrangement for the purification steps that may be used in step (c) in the process of the invention.

Figure 1:
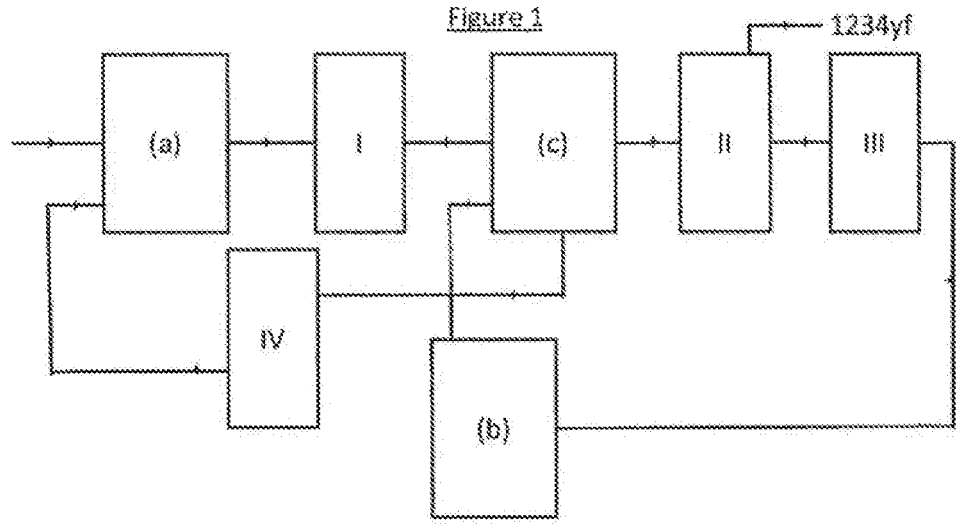
FIG. 1. provides a schematic representation of a process of the invention.

In FIG. 2, where a reference symbol corresponds to a reference symbol used in FIG. 1, it has the same meaning as in FIG. 1.

In the configuration for step (c) shown in FIGS. 2, Y and Z are distillation steps and X is a scrubbing train, $X^1$, $X^2$ and $X^3$ are scrubbers within the scrubbing train. As an example, $X^1$ may be a water scrubber, $X^2$ may be a basic scrubber, such as a KOH scrubber and $X^3$ may be an acid scrubber such as a $H_2SO_4$ scrubber. In distillation step Y, lighter/lower boiling components of the feed mixture (including 245cb, 1234yf, 1234ze(E) and some HF) are distilled from the mixture leaving a heavier/higher boiling fraction (including the majority of the HF and unreacted 1233xf). The distillate is passed to the scrubbing train X. The scrubbing train removes effluent. The product stream leaving the scrubbing train comprises 1234yf, 245cb, and low boiling impurities such as TFMA. The distillation still Z may be used to remove low boiling impurities such as TFMA.

For the sake of simplicity, in FIGS. 1 and 2, only the key inlet and product streams have been included.

The invention claimed is:

1. An integrated process for preparing 2,3,3,3-tetrafluoropropene (1234yf), the process comprising:
   (a) vapour phase catalytic fluorination of a first composition comprising 3,3,3-trifluoro-2-chloro-prop-1-ene ($CF_3CCl=CH_2$, 1233xf) with hydrogen fluoride (HF) in a fluorination reactor to produce a fluorination product stream comprising 1,1,1,2,2-pentafluoropropane (245cb), HF and HCl;
   (b) vapour phase catalytic dehydrofluorination of a second composition comprising 245cb in a dehydrofluorination reactor to produce a dehydrofluorination product stream comprising 1234yf and HF;
   wherein the fluorination product stream and the dehydrofluorination product stream are combined and subjected to (c) purification to produce a composition comprising 245cb and a 1234yf product stream,
   wherein the purification step (c) comprises a distillation step in which a lighter fraction comprising 245cb, 1234yf, any 1234ze(E) and some HF is distilled leaving a heavier fraction comprising the majority of the HF and unreacted 1233xf, and wherein the lighter fraction is removed from the distillation column and passed to a scrubbing train.

2. A process according to claim 1, wherein the composition comprising 245cb and a 1234yf product stream is fed to the dehydrofluorination reactor as the second composition.

3. A process according to claim 1, in which at least some of the 1234yf is removed from the composition comprising 245cb and a 1234yf product stream and the resulting composition is fed to the dehydrofluorination reactor as the second composition.

4. A process according to claim 3, wherein after at least some of the 1234yf has been removed, the resulting composition is subjected to a purification step in which at least some of any 1234ze that may be present in the composition is removed before the composition with reduced 1234yf concentration is fed to the dehydrofluorination reactor as the second composition.

5. A process according to claim 1, wherein the purification step (c) comprises one or more phase separation steps.

6. A process according to claim 1, wherein the scrubbing train in the purification step (c) comprises in sequence a bulk acid removal step, a trace acid removal step and one or more drying steps.

7. A process according to claim 1 wherein HF is recovered from at least one distillation column and is optionally recycled for use in reaction (a).

8. A process according to claim 7, wherein the HF is subjected to further purification prior to recycling.

9. A process according to claim 8, wherein the HF is purified by phase separation.

10. A process according to claim 1, wherein the process comprises a step of obtaining the 1233xf used in reaction (a) by the dehydrochlorination of 243db.

11. A process according to claim 10, wherein the dehydrochlorination reaction takes place in the presence of HF and/or in the absence of air.

12. A process according to claim 10, wherein the dehydrochlorination reaction takes place in the presence of a zinc/chromia catalyst.

13. A process according to claim 10, wherein the dehydrochlorination reaction takes place in the presence of HF and at least part of the HF is recycled from step (c).

14. A process according to claim 1, wherein reaction (a) takes place in the presence of air.

15. A process according to claim 14, wherein the fluorination product stream is subjected to a purification step to remove at least some of the HCl and at least some of the air before this product stream is combined with the dehydrofluorination product stream.

16. A process according to claim 15, wherein distillation is used to remove at least some of the HCl and at least some of the air.

17. A process according to claim 1, wherein reaction (a) takes place in the presence of a zinc/chromia catalyst.

18. A process according to claim 1, wherein reaction (b) takes place in the presence of a chrome on alumina or zinc/chromia catalyst.

19. A process according to claim 1, wherein reaction (a) takes place at a temperature of from about 200 to about 300° C. and a pressure of from about 500 to about 1500 KPa.

20. A process according to claim 1, wherein reaction (b) takes place at a temperature of from about 300 to about 500° C. and/or a pressure of from about 0 to 1500 kPa.

* * * * *